United States Patent
Shah et al.

(10) Patent No.: US 12,023,077 B2
(45) Date of Patent: *Jul. 2, 2024

(54) FRACTURE PLATE

(71) Applicants: Anup A. Shah, Sugar Land, TX (US); Joshua T. Woody, Houston, TX (US)

(72) Inventors: Anup A. Shah, Sugar Land, TX (US); Joshua T. Woody, Houston, TX (US)

(*) Notice: Subject to any disclaimer, the term of this patent is extended or adjusted under 35 U.S.C. 154(b) by 367 days.

This patent is subject to a terminal disclaimer.

(21) Appl. No.: 17/222,332

(22) Filed: Apr. 5, 2021

(65) Prior Publication Data

US 2021/0220032 A1 Jul. 22, 2021

Related U.S. Application Data

(60) Continuation of application No. 16/361,162, filed on Mar. 21, 2019, now Pat. No. 10,966,766, which is a division of application No. 14/692,995, filed on Apr. 22, 2015, now Pat. No. 10,238,438.

(51) Int. Cl.
*A61B 17/80* (2006.01)
*A61B 17/86* (2006.01)
*A61B 17/88* (2006.01)

(52) U.S. Cl.
CPC .......... *A61B 17/8061* (2013.01); *A61B 17/86* (2013.01); *A61B 17/8894* (2013.01); *A61B 17/8897* (2013.01); *A61B 17/8014* (2013.01); *A61B 17/8052* (2013.01)

(58) Field of Classification Search
CPC ...................... A61B 17/80–17/8095
See application file for complete search history.

(56) References Cited

U.S. PATENT DOCUMENTS

| | | | | |
|---|---|---|---|---|
| 6,096,040 | A | * | 8/2000 | Esser ................. A61B 17/8061 606/280 |
| 6,645,210 | B2 | * | 11/2003 | Manderson ............ A61B 17/80 606/902 |
| 6,712,073 | B2 | * | 3/2004 | Manderson ............ A61B 17/80 606/281 |
| 7,655,029 | B2 | * | 2/2010 | Niederberger ..... A61B 17/8061 606/280 |
| 9,283,008 | B2 | * | 3/2016 | Gonzalez-Hernandez ................. A61B 17/8061 |
| 2004/0092935 | A1 | * | 5/2004 | Manderson ............ A61B 17/80 606/907 |
| 2007/0043368 | A1 | * | 2/2007 | Lawrie ................. A61B 17/809 606/291 |
| 2007/0123880 | A1 | * | 5/2007 | Medoff .............. A61B 17/8085 606/326 |
| 2011/0160730 | A1 | * | 6/2011 | Schonhardt .......... A61B 17/085 606/71 |
| 2011/0313422 | A1 | * | 12/2011 | Schwager .......... A61B 17/8057 606/71 |
| 2012/0226323 | A1 | * | 9/2012 | Gonzalez-Hernandez ................. A61B 17/8061 606/286 |
| 2014/0172020 | A1 | * | 6/2014 | Gonzalez-Hernandez ................. A61B 17/8085 606/280 |

* cited by examiner

*Primary Examiner* — Zade Coley
(74) *Attorney, Agent, or Firm* — Whittaker Law Firm; Malcolm E. Whittaker

(57) ABSTRACT

A method of promoting healing of a fracture of a human humerus using a proximal humeral fracture plate.

19 Claims, 14 Drawing Sheets

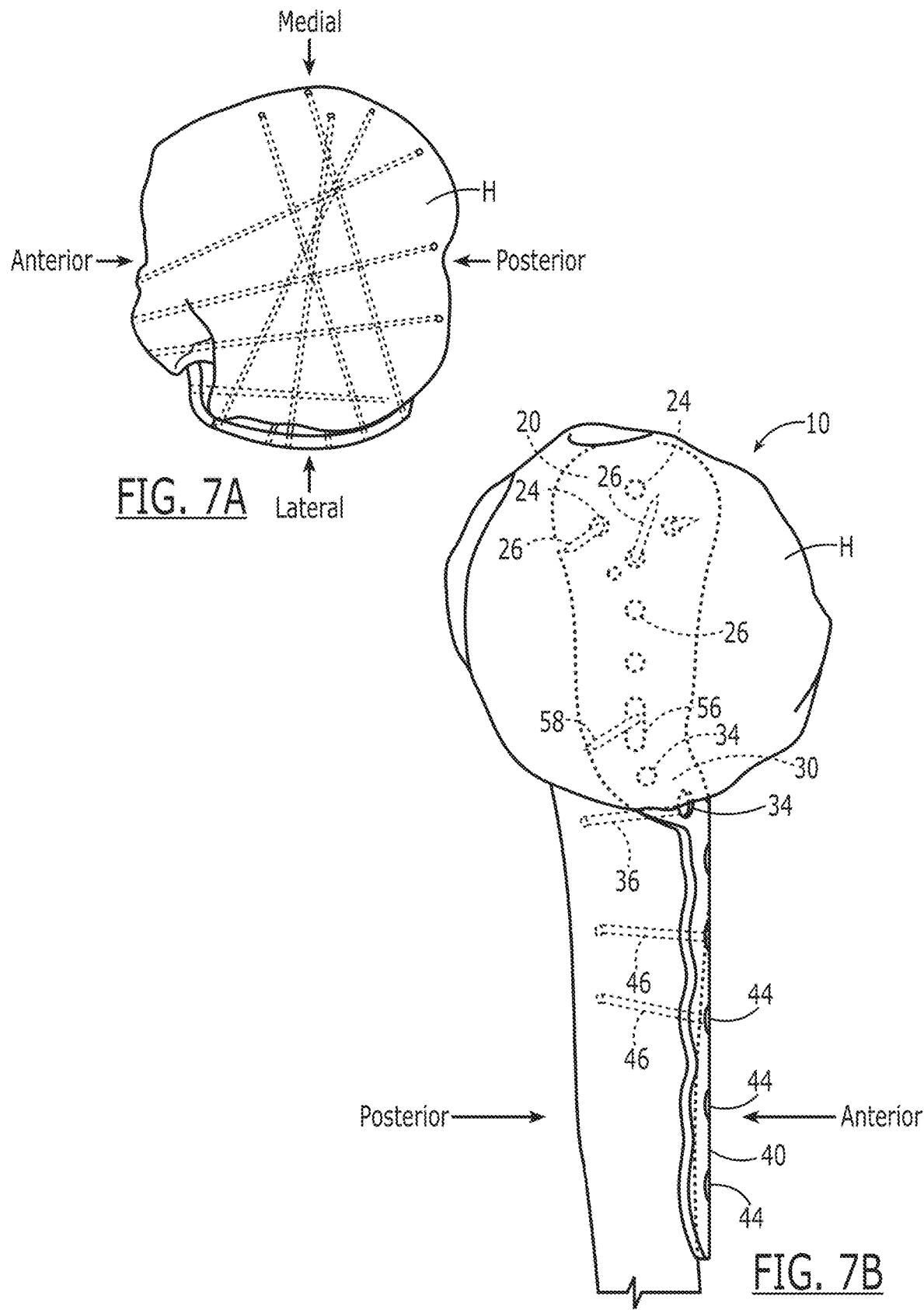

FRACTURE PLATE

CROSS-REFERENCE TO RELATED APPLICATIONS

The present application is a continuation of U.S. Utility patent application Ser. No. 16/361,162, filed on Mar. 21, 2019, which is expected to issue on Apr. 6, 2021, which in turn was a divisional application of U.S. Utility patent application Ser. No. 14/692,995, also titled Proximal Humeral Fracture Plate, and filed on Apr. 22, 2015 and now issued as U.S. Pat. No. 10,238,438.

STATEMENT REGARDING FEDERALLY SPONSORED RESEARCH

Not Applicable.

BACKGROUND OF THE INVENTION

Proximal humeral fractures represent about 4-5% of all fractures and represent the third most common fracture among older patients. In many patients, the proximal humeral fracture most typically results from a fall. The damage to the humerus can be compounded by osteoporosis or an otherwise weakened bone that is found more frequently in older female patients. In younger patients, proximal humeral fractures are more likely to be a result of high-energy trauma; such as an automobile accident or a sporting injury.

The majority of proximal humeral fractures are minimally or non-displaced and are generally treated non-operatively.

However, operative fixation is indicated in displaced, angulated and rotated fracture patterns. Among the operative solutions commonly used for fixation are: (1) osteosuture and tension band technologies; (2) percutaneous fixation using pins and wires; (3) rigid intramedullary nailing (e.g., using a large rod inside the bone); (4) plate osteosynthesis (e.g., using open reduction internal fixation using plate(s) and screws); (5) arthroplasty (e.g. using a prosthesis to replace a broken portion of a humerus); and, other indication-specific techniques.

There are two primary categories for surgical fixation: (1) a device that is within the skin (internal fixation); and (2) a device that extends out of the skin (external fixation). There are two common types of internal fixation approaches for long bone surgery: (a) a plate that is screwed to the outside of the bone; or (b) a rod that goes down the center of the bone.

Current plate technology uses straight, also referred to as linear, plates, as illustrated in FIG. 1B. For example, U.S. Pat. No. 6,096,040, issued to Esser, on Aug. 1, 2000, claims a linear bone plate. Additional examples of current proximal humeral plates are the Stryker AxSOS Locking Plating System, produced by Stryker Trauma AG at least as early as 2011. The Zimmer Periarticular Locking Plate, produced by Zimmer at least as early as 2006 are both examples of currently available linear plating systems. These straight plates limit the trajectory of the screws within the humeral head, which has been found to be problematic.

As illustrated in FIG. 1A, a humerus H is part of a human skeleton S. FIG. 1B illustrates a current linear bone plate. FIG. 2 illustrates the humerus H separated from skeleton S. The shaft of a long bone, such as the humerus H, is typically classified as the diaphysis. The end of such a bone is typically classified as the epiphysis. Bone that is transitional between the midshaft and the end is typically classified as the metaphysis.

Metaphysis and epiphysis bone are softer and more porous. The bone of the metaphysics and epiphysis is less dense than the diaphysial bone of the shaft. Since metaphysical and epiphyseal bone are cancellous bone, they are more affected by osteoporosis. Repair of metaphysis and epiphysis fractures are often complicated by their proximity to a joint. Due to the bone quality and anatomic shapes of the metaphyseal and epiphyseal bone, fixation of plates and screws in these areas is typically more difficult than fixation of plates and screws in diaphysis shaft. This may be especially true if the patient is elderly and suffers from osteoporosis. Thus, proper placement of screws in epiphysis and metaphysis bone is desirable to obtain appropriate fixation of a plate. Phrased differently, a current linear plate may obtain good fixation to the diaphysis, but fail to obtain appropriate fixation to the epiphysis and metaphysis.

While not every proximal humeral fracture is the same, the Neer system of proximal humeral fractures is based on four parts of the humerus. The four parts are as follows:
(I) fracture of the greater tuberosity;
(II) fracture of the lesser tuberosity;
(III) fracture of the humeral head; and,
(IV) fracture of the neck.

According to Neer, a fracture is displaced when there is more than 1 cm (one centimeter) of displacement and/or 45° of angulation of any one fragment with respect to the others.

Two-part fractures involve any of the 4 parts and include 1 fragment that is displaced. Three-part fractures include a displaced fracture of the surgical neck in addition to either a displaced greater tuberosity or lesser tuberosity fracture. Four-part fractures include displaced fractures of the surgical neck and both tuberosities.

FIG. 3 is a chart of the Neer system of classifying displaced proximal humeral fractures. Fractures of the proximal humerus typically follow these fracture lines. With this said, humerus H can fracture in patterns not illustrated in FIG. 3 and the Neer system is merely a way of classifying fractures. For example, humerus H may suffer complex fractures that extend into the shaft, both above and below the deltoid insertion. The Neer system may be thought of as helping surgeons to identify patients that likely would benefit from surgery. It does not determine the type of surgical intervention that might be medically beneficial.

Currently, surgeons find it problematic to use existing linear proximal plates to resolve these issues. If a surgeon has identifies a fracture that meets the indications for surgery then one of the options noted above could be used. If a surgeon selects Open-Reduction Internal Fixation (ORIF), a surgical plate could be medically beneficial.

FIG. 4 illustrates X-rays of a current linear plate fixed to a patient's humerus. FIG. 4 further illustrates the linearality of the current plates. Use of the current linear plate will produce sub-optimal screw trajectory within the humeral head. If the surgeon attempts to position the distal section of the current linear plate sufficiently anterior to avoid the deltoid tuberosity, the proximal head of the plate will be correspondingly moved anterior. This de-optimizes screw trajectory within the humeral head. Obviously, poor screw placement, likely results in sub-optimal fixation of the current linear plate to the humerus H, and particularly to the head of humerus H. Phrased differently, and as illustrated in FIG. 4, the screws fixing current linear plates to the humeral head obtain less purchase than is optimal. Screw trajectories that pass through more bone are generally thought to obtain better purchase, also referred to as fixation, to the bone, including bone of the humeral head. Generally speaking because of the shape of the humeral head, screw trajectories through the humeral head are preferred to be in the lateral to medial orientation to optimize fixation of the plate and screws. With current plates, to avoid disruption of the deltoid insertion and the deltoid tuberosity, the plate is placed more anterior than is optimal. As the plate is placed more anteriorly, the screws are more in the posterior surface of the humerus. This results in the screws in the humeral head being oblique, and results in screws that don't obtain appropriate fixation in the anterior portion of the humeral head.

Current linear plates have various issues. First, installation of the current linear plates can require significant removal of the deltoid tuberosity and detachment of the deltoid. Second, not all fractures will heal. If the fracture is treated with open reduction internal fixation with a plate, and the bone fails to heal appropriately, then a reverse total shoulder arthroplasty may be the appropriate treatment. A reverse total shoulder arthroplasty employs the intact function of the deltoid. Detachment of the deltoid can preclude use of a reverse total shoulder arthroplasty, in the event of the failure of surgery using the current plate to appropriately resolve the fracture of the humerus because of the fracture failing to heal. Third, and as discussed above, if the surgeon attempts to position the distal section of the current linear plate sufficiently anterior to avoid the deltoid tuberosity, the proximal head of the plate will be correspondingly moved anteriorly. This de-optimizes screw trajectory within the humeral head. Poor screw placement likely results in sub-optimal fixation of the current linear plate to the humerus, and particularly to the head of humerus. Fourth, current plates typically have screw trajectories that run obliquely thought the humeral head from anterolateral to posteromedial, rather than the more optimal true lateral to medial within the head. Current plates have all of the screw trajectories in essentially a single plane. Screw trajectories in more than one plane will provide greater strength and improved plate fixation.

Current plates are linear, and only provide fixation in essentially a single plane. When current plates are placed anterior to the deltoid insertion, the screws have a poor trajectory within the humeral head. With anterior plate positioning, the screw trajectory limits screw fixation in the anterior portion of the humeral head, which is sub-optimal. When the current plates are placed laterally, the plates damage the deltoid insertion, where the deltoid muscle attaches to the humerus.

The plate that is the subject of this patent application curves around the humerus where the proximal portion of the plate is on the lateral surface of the humeral head and the distal portion of the plate is on the anterior surface of the humeral shaft. The screws through the proximal portion have a true lateral to medial direction within the humeral head. This lateral to medial screw trajectory in the humeral head gives more optimal fixation by allowing screws be placed throughout the humeral head. The plate that is the subject of this patent application also has screws through the distal portion that have a trajectory in an anterior to posterior direction in the humeral shaft. The plate that is the subject of this patent application allows for the screws to obtain fixation in multiple planes. The curve of the plate allows the plate to avoid the deltoid tuberosity avoiding damage to the deltoid tendon and the deltoid insertion of the deltoid tuberosity. The curved portion also allows for oblique screws within the humeral metaphysis. The oblique metaphysis screws compliment the lateral to medial screws within the humeral head. The lateral to medial screw trajectory optimizes screw fixation within humeral head, while preserving the attachment of the deltoid muscle. In addition, the configuration allow the plate to extend down the entire length of the humerus allowing the plate to treat more complex fractures that extend into the humeral shaft without compromising the deltoid and avoiding potential damage to nerves, such as the radial nerve.

SUMMARY OF THE INVENTION

A method of promoting healing of a fracture of a human humerus using a proximal humeral fracture plate, comprising: fixing the proximal humeral fracture plate to the humerus, wherein the proximal humeral fracture plate comprises: (a) an upper section having at least one screw hole for receiving an upper screw, the trajectory of the screw hole is a lateral to medial orientation; (b) an anteriorly curved section having a plurality of screw holes for receiving a plurality of middle screws, the anteriorly curved section integral with the upper section and curvedly configured to avoid the deltoid tuberosity, the screw hole therethrough the anteriorly curved section having an oblique trajectory relative to the trajectory of the screw hole of the upper section and configured to match an anatomy of a lateral cortex of the humerus, wherein the screw holes therethrough the anteriorly curved section each have a more anterior to posterior trajectory than the screw hole therethough the anteriorly curved section above it; and, a lower section having at least one screw hole for receiving a lower screw, the trajectory of the screw hole having an oblique trajectory relative to the trajectory of the screw holes of the anteriorly curved section, the lower section integral with the anteriorly curved section.

These and other embodiments will be more fully appreciated from the description below.

BRIEF DESCRIPTION OF THE DRAWINGS

FIG. 7A is a superior view of the proximal humeral fracture plate for repairing a fracture of a patient's left humerus.

FIG. 7B is a perspective view of the proximal humeral fracture plate shown in FIG. 7A. An upper section of the proximal humeral fracture plate shown in FIG. 7A is illustrated in dashed lines.

DESCRIPTION OF THE PREFERRED EMBODIMENTS

Corresponding reference numbers indicate corresponding parts throughout the several views of the drawings and specification. Corresponding reference numbers indicate corresponding parts throughout the several views of the drawings and specification.

Figure 1A:
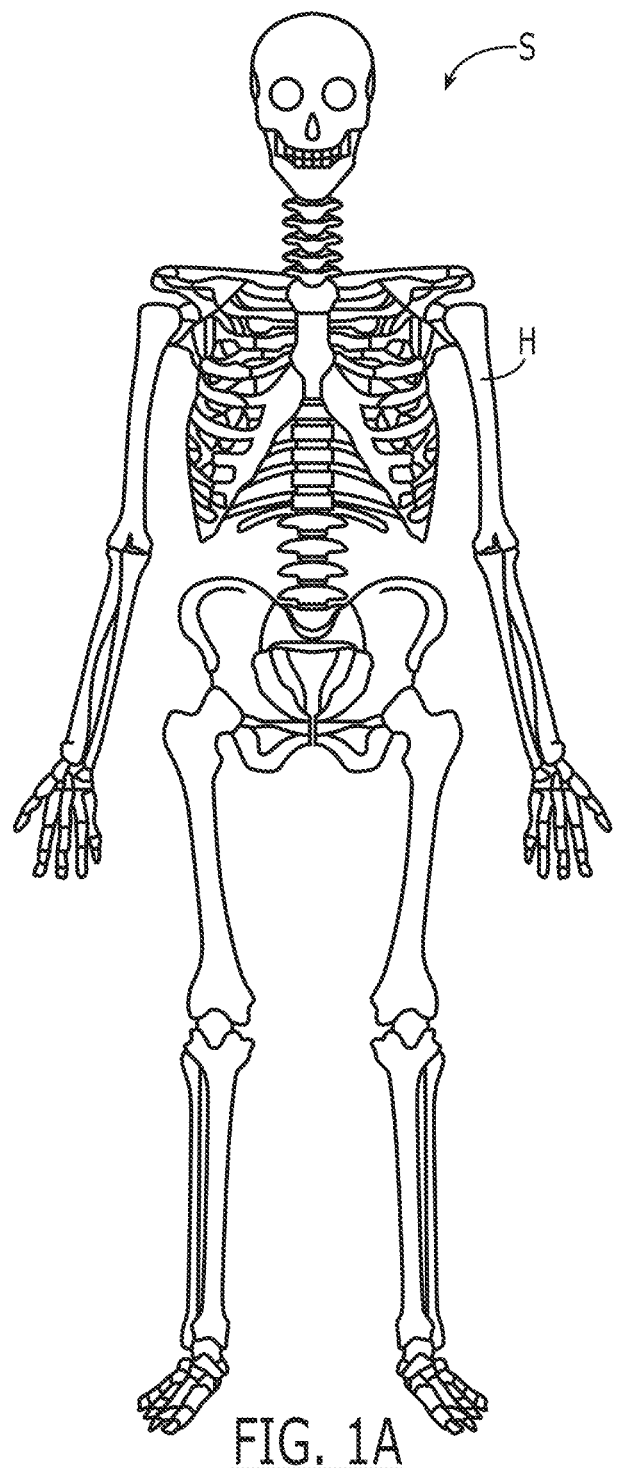
FIG. 1A is a front view of a human skeleton.
Figure 1B:
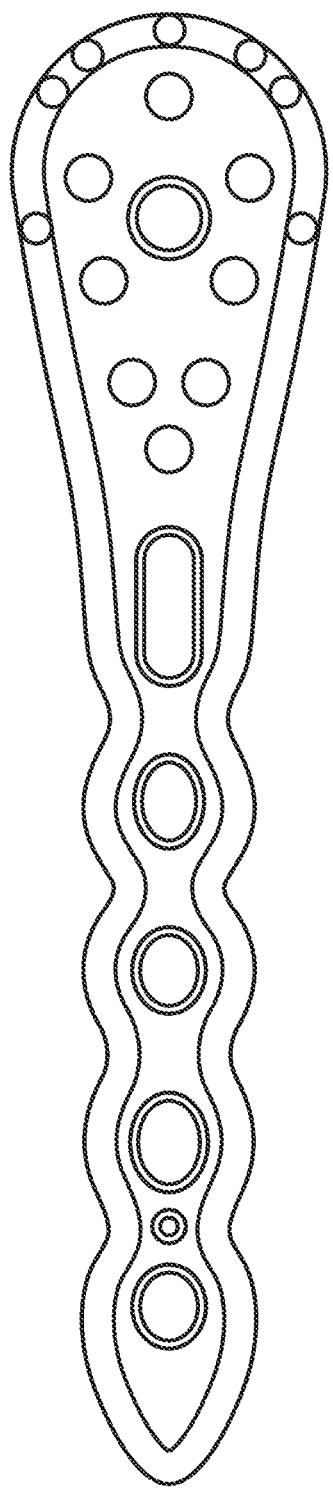
FIG. 1B is a front view of a prior art current linear bone plate.
Figure 2:
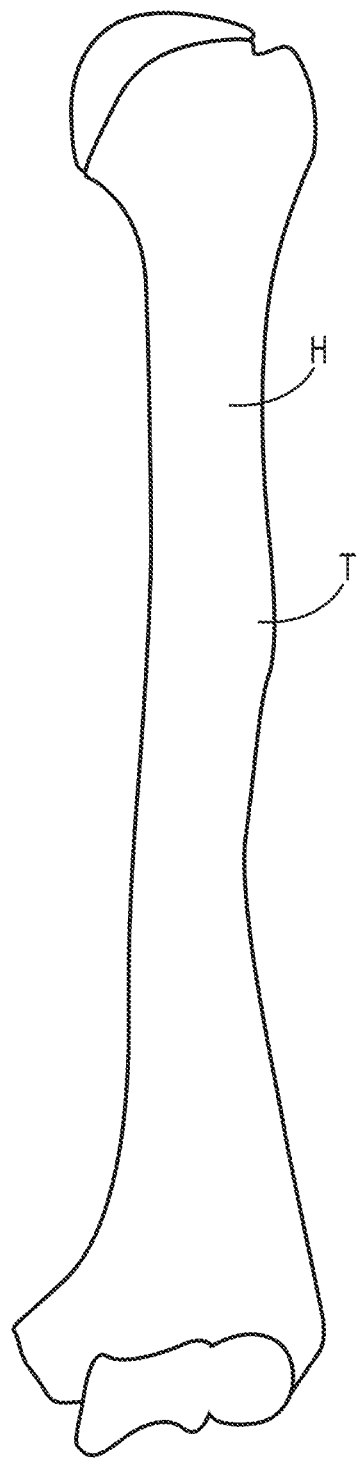
FIG. 2 is a perspective view of a human humerus.
Figure 3:
FIG. 3 is a chart of the Neer system of classifying displaced proximal humeral fractures.
Figure 4:
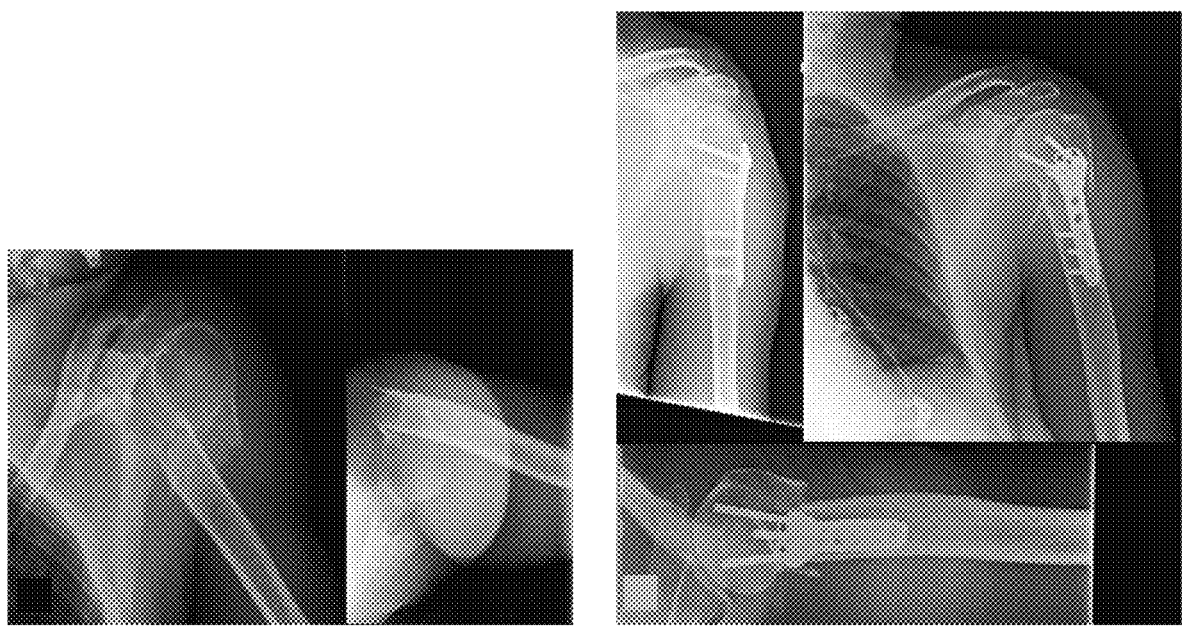
FIG. 4 are X-rays of a current linear plate installed in a patient.
Figures 5A, 5B:
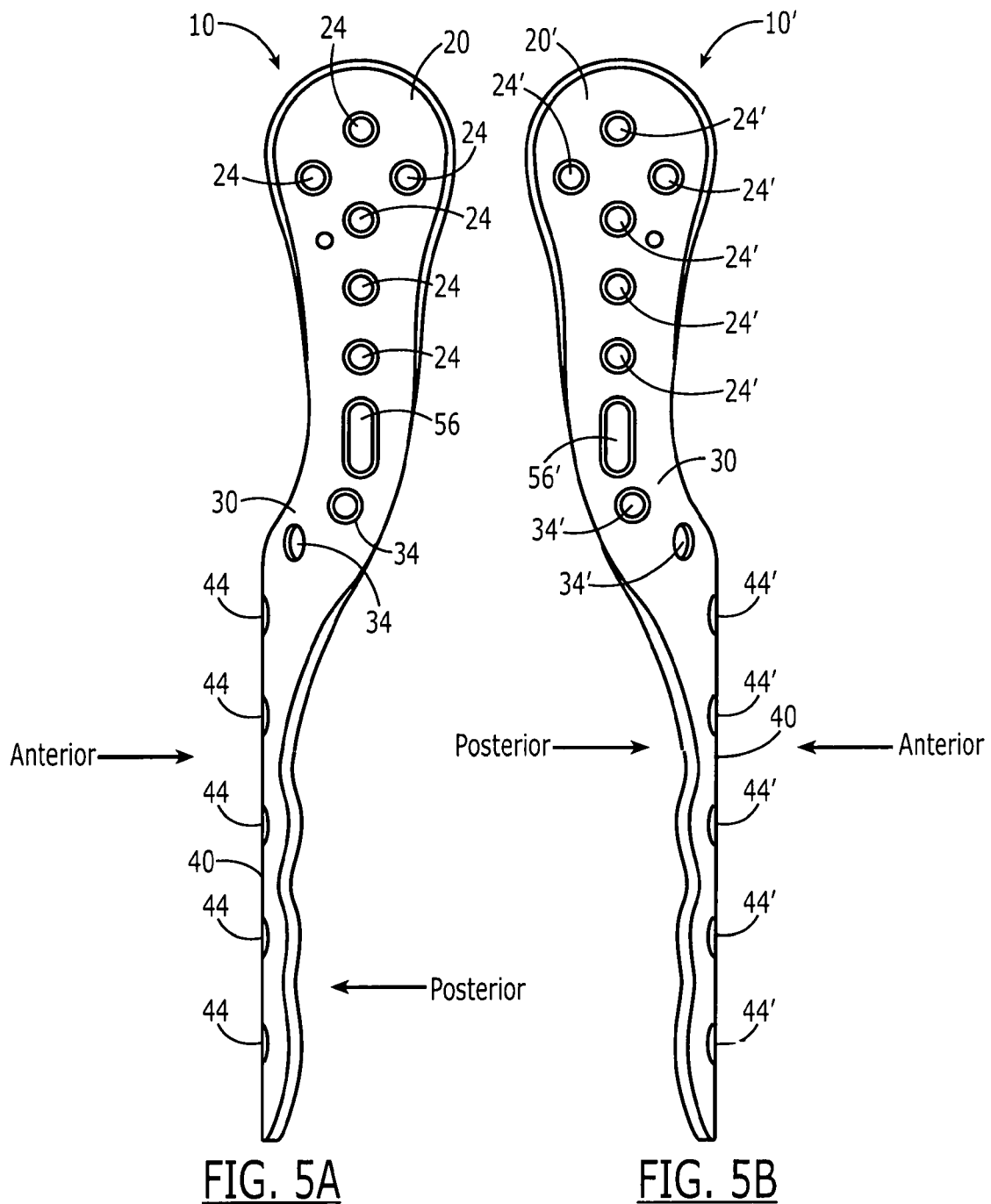
FIG. 5A is a lateral view of a proximal humeral fracture plate for repairing a fracture of a patient's left humerus.
FIG. 5B is a lateral view of a proximal humeral fracture plate for repairing a fracture of the patient's right shoulder.

FIG. 5A illustrates a proximal humeral plate 10 for use on a patient's left shoulder. An upper section 20 has a screw hole 24 for receiving a screw to fix the proximal humerus plate to a head of the left humerus H. The trajectory of the screw hole 24 is a lateral to medial orientation. A transitional section 30 has holes 34 for receiving a screw 36 (not shown) to fix the transitional section along a lateral cortex of the humerus H. Transitional section 30 is integral with the upper section 20 and is curved sufficiently to avoid a deltoid tuberosity T (seen in FIG. 2). A lower section 40 has screw holes 44 for receiving a screw 46 (not shown), the trajectory of screw hole 44 is an anterior to posterior orientation. Lower section 40 is integral with the transitional section 30. Preferably, plate 10 should be fixed to the shaft of humerus H distally using a non-locking screw through hole 56. Preferably, hole 56 should be oblong to permit plate 10 to slide proximally or distally along humerus H before a screw 58 (not shown) is fully tightened to hold plate 10 in position. In other words, the non-locking screw 58 would compress plate 10 to humerus H to provide provisional fixation of plate 10. It is preferable to compress plate 10 to humerus H such that there is no gap between humerus H and plate 10 and non-locking screws are preferred to compress plate 10 to humerus H. It has been found that surgeons may inadvertently fix plate 10 to humerus H with a gap between plate 10 and humerus H. This is undesirable and should be avoided. It has also been found that Kirschner wires [not shown] can be used to provisionally position plate 10. Preferably, after plate 10 has been provisionally fixed to humerus H, locking screws will be used to fix plate 10 to humerus H.

FIG. 5B illustrates a proximal humeral plate 10' for use on a patient's right shoulder. Unlike linear plates, which are used for both the left and right humerus, plate 10' is specific for use to the right shoulder and is, preferably, a mirror image of plate 10. An upper section 20' has screw hole 24' for receiving a screw 26' (not shown) to fix the proximal humerus plate to a head of the right humerus H. As with plate 10, the trajectory of screw hole 24' for plate 10' is a lateral to medial orientation. A transitional section 30' has screw holes 34' for receiving a screw 36' to fix transitional section 30' along a lateral cortex of the right humerus H. Transitional section 30' is integral with the upper section 20' and curves sufficiently to avoid a deltoid tuberosity T. A lower section 40' has screw holes 44' for receiving a screw 46'. As with plate 10, the trajectory of screw hole 44' for plate 10' is an anterior to posterior orientation. Lower section 40' is integral with the transitional section 30'. Preferably, plate 10' should be fixed to the shaft of humerus H distally using a non-locking screw 58' (not shown) through hole 56'. Preferably, hole 56' should be oblong to permit plate 10' to slide proximally or distally along humerus H before screw 58' is fully tightened to hold plate 10' in position. In other words, the non-locking surgical screw 58' would provisionally fix plate 10' to right humerus H to provide provisional fixation of plate 10' to humerus H and thereby hold plate 10' against humerus H. It is preferable to compress plate 10' to humerus H such that there is no gap between humerus H and plate 10' and non-locking screw 58' are preferred to compress plate 10' to humerus H. It has been found that surgeons may inadvertently fix plate 10' to humerus H with a gap between plate 10' and humerus H. As discussed above, this is undesirable and should be avoided. As also discussed above, preferably, after plate 10' has been provisionally fixed to humerus H, locking screws will be used to fix plate 10 to' humerus H.

Preferably, non-locking screws should be used in oval screw holes and locking screws should be used with circular screw holes.

Figures 5C, 5D:
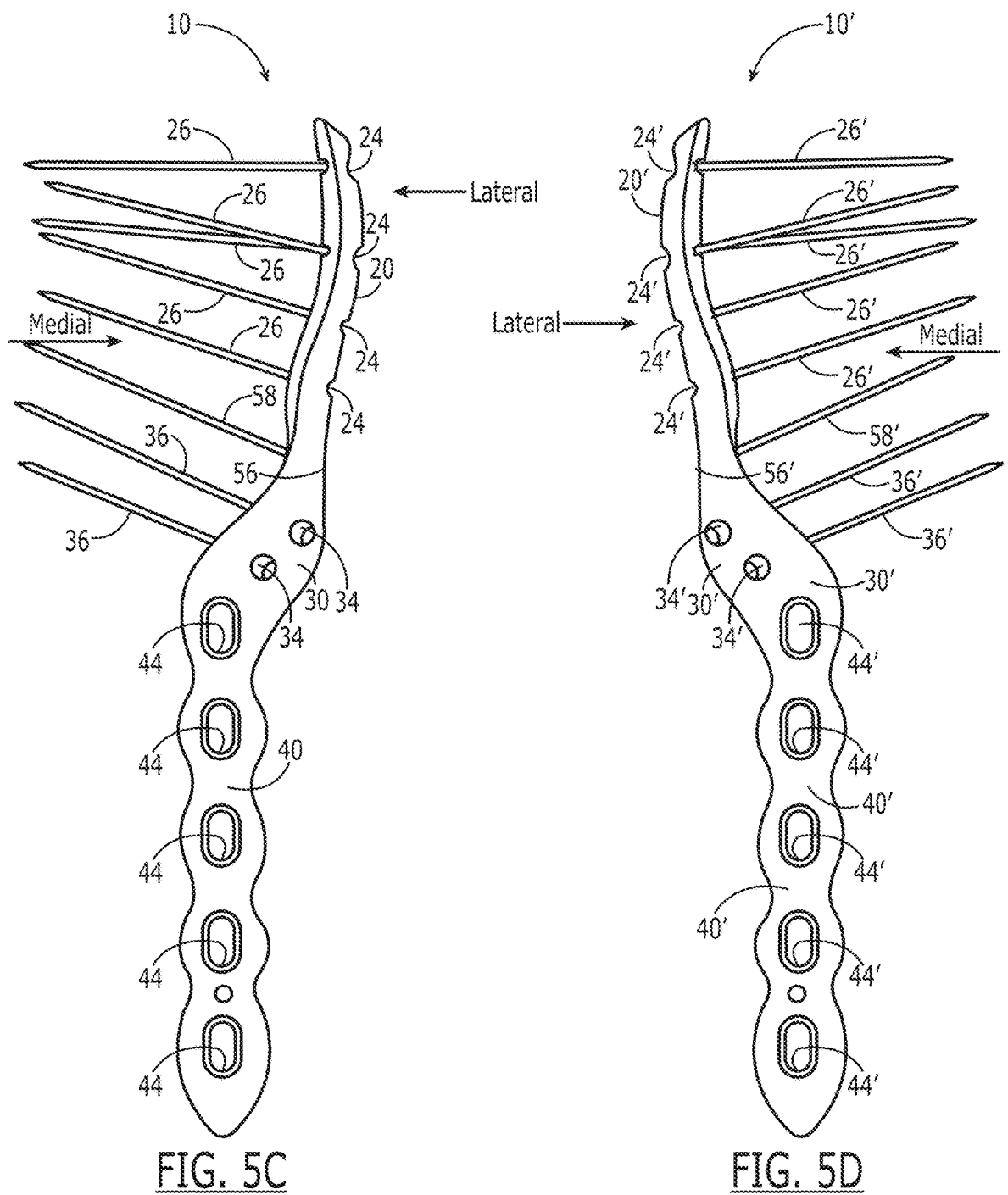
FIG. 5C is an anterior view of the proximal humeral fracture plate of FIG. 5A.
FIG. 5D is an anterior view of the proximal humeral fracture plate of FIG. 5B.

FIG. 5C illustrates plate 10 with screws 26 and 36 inserted into holes 24 and 34, respectively. As discussed above, the trajectory of the screws 26 for holes 24 is a generally lateral to medial orientation. Phrased differently, screws 26 transit the head of humerus H in a generally lateral to medial orientation. As also discussed above, the trajectory of screws 36 fixes the transitional section 30 of plate 10 along a lateral cortex of the humerus H. Screws 46 are inserted into holes 44 and have a generally anterior to posterior trajectory.

FIG. 5D illustrates plate 10' with surgical screws 26' and 36' inserted into holes 24' and 34', respectively. As discussed above, the trajectory of the screws for holes 24' is a generally lateral to medial orientation. As also discussed above, the trajectory of screws 36' fixes the transitional section 30' of plate 10' along a lateral cortex of the humerus H. Screws 46' are inserted into holes 44' and have a generally anterior to posterior trajectory.

Figure 5F:
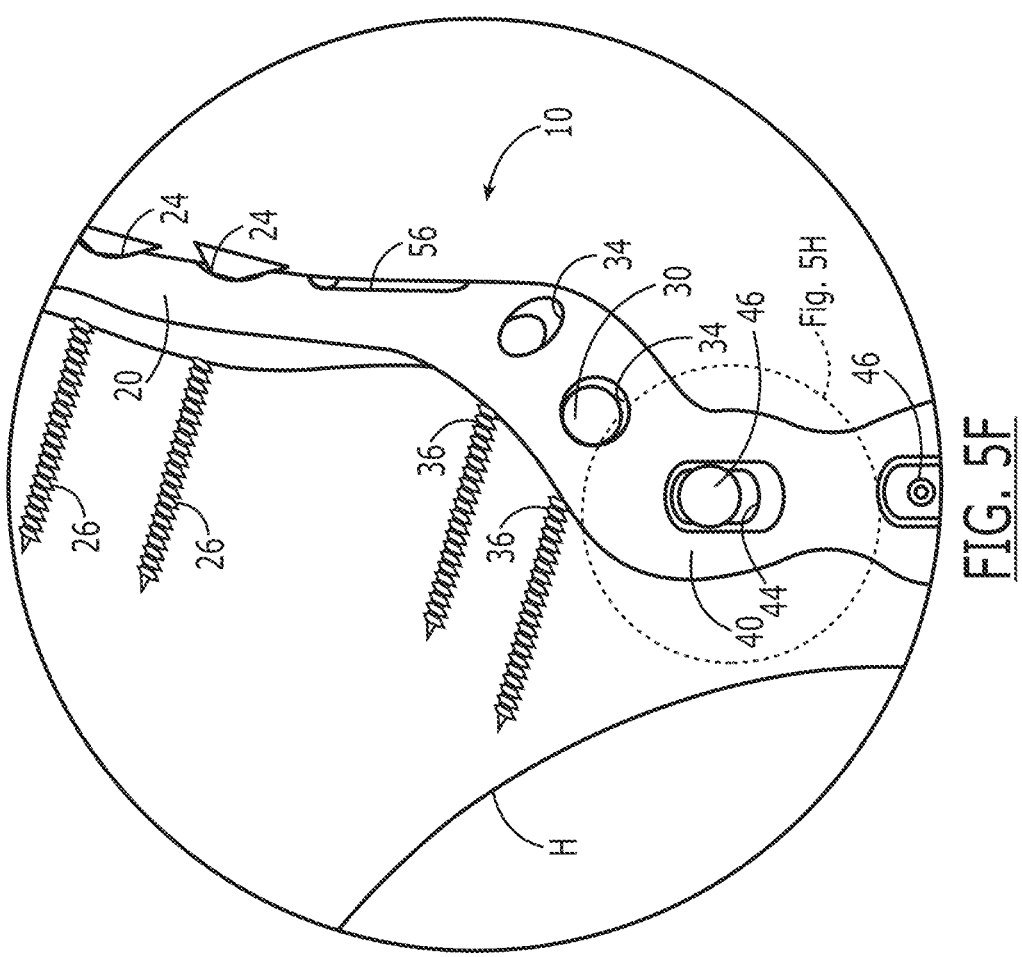
FIG. 5F is a detailed view of a transitional section of the proximal humeral fracture plate shown in FIGS. 5A and 5C.
Figure 5E:
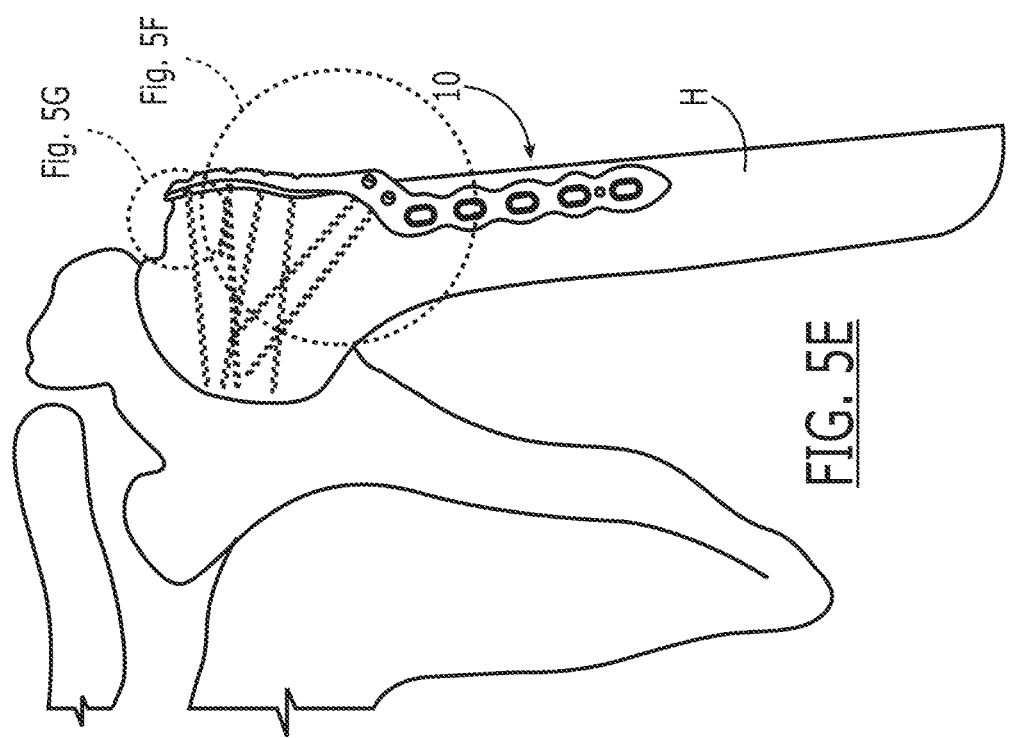
FIG. 5E is an anterior view of the proximal humeral fracture plate of FIGS. 5A and 5C fixed to the patient's left humerus.

FIG. 5E illustrates plate 10 fixed to left humerus H. For purposes of the present application, both the left humerus and the right humerus are referred to as humerus H. Screws 26 and 36 (shown in dashed lines) are inserted into holes 24 and 34 to fix plate 10 to humerus H. FIG. 5E also illustrates that upper section 10 is fixedly attached to the head of humerus H. Optimally, upper section 20 would start just distal to the tip of the greater tuberosity (seen in FIG. 2) and would run along the lateral cortex of humerus H to allow for lateral to medial screw placement in the head of humerus H. Plate 10 would then curve anteriorly such that transitional section 30 would avoid deltoid tuberosity T. Transitional section 30 is fixed to the distal portion of humerus H. As illustrated in FIG. 5D, transitional section 30 would curve plate 10 anteriorly to avoid damage to the deltoid tuberosity T. Alternatively, the deltoid tuberosity T may also be referred to as the deltoid insertion. Irrespective of which word is used to describe this boney structure, the tuberosity T is where the deltoid muscle attaches to the humerus H. FIG. 5E also illustrates that upper section 20 is fixed to the head of humerus H and that the trajectory of screws 26 passing through upper section 20 are in a lateral to medial orientation. FIG. 5E also illustrates transitional section 30. Transitional section 30 has screw holes 34 for receiving screws 36 to fix the transitional section along a lateral cortex of the humerus H. Transitional section 30 is integral with the upper section 20 and is curved sufficiently to avoid a deltoid tuberosity T. Lower section 40 has screw holes 44 for receiving screws 46 (not shown), the trajectory of the screws are in an anterior to posterior orientation. Lower section 40 is integral with the transitional section 30.

FIG. 5F illustrates a detailed view of transitional section 30 curving anteriorly to avoid damage to the deltoid insertion. A portion of lower section 40 is illustrated and screw 46 and screw hole 44 can be seen in FIG. 5F. FIG. 5F also illustrates screw holes 34 therethrough transitional section 30. Screws 36 fix transitional section 30 along the lateral cortex of the humerus H and support bone repair and healing.

Figure 5G:
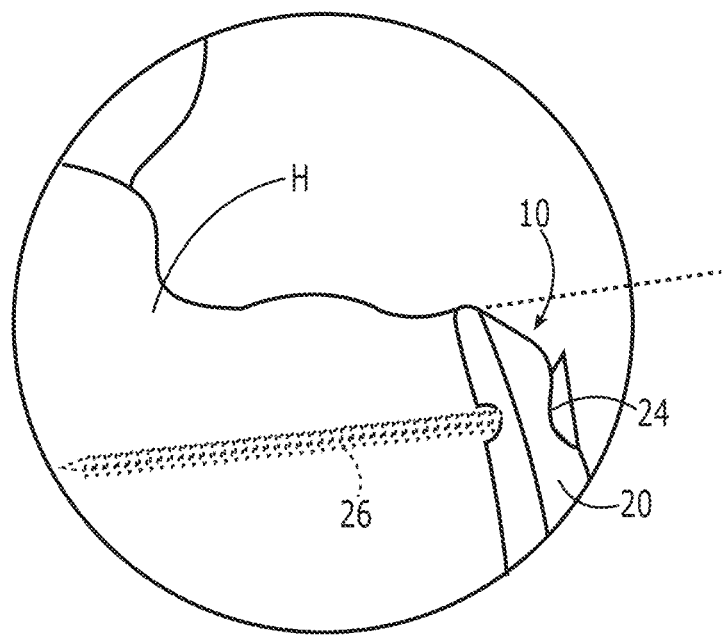
FIG. 5G is a detailed view of the upper section of the proximal humeral fracture plate shown in FIG. 5E.

FIG. 5G also illustrates an imaginary dashed line reflecting that plate 10 is preferably positioned such that the top of upper section 20 is flush with the top of humerus H and does not project above the top of humerus H. If this misplacement occurs, plate 10 may impinge on the patient's acromion. This is undesirable because it may prevent appropriate rotation of the patient's arm or damage the patient's acromion or other tissue. It can result in patient pain or discomfort and also limit the range of motion of the patient's shoulder. These are undesirable outcomes.

Figure 5H:
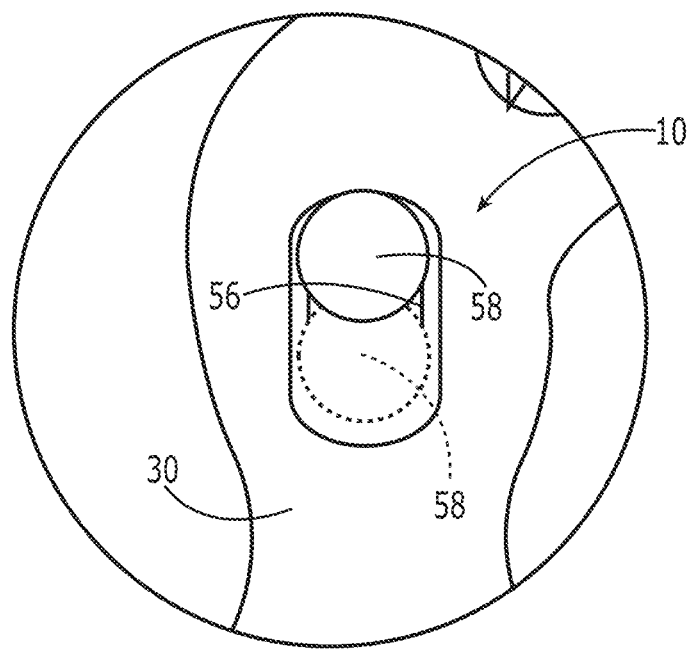
FIG. 5H is a detailed view of the transitional section of the proximal humeral fracture plate shown in FIG. 5F.

FIG. 5H illustrates that hole 56 of plate 10 can be used to adjust the position of plate 10 upwardly or downwardly before fixation of plate 10 to humerus H. For example, when initially placed, plate 10 might be located such that the top of upper section 20 projects above the top of humerus H. As discussed above, this is undesirable. Screw 58 is shown in dashed lines to reflect the relative positions of plate 10 and screw 58 in this undesirable plate placement. If this situation occurs, the surgeon would likely elect to slide plate 10 downwardly until the top of upper section 20 is flush with the top of humerus H, as seen in FIG. 5G, and does not project above the top of humerus H. For example, after plate 10 is slide downwardly, screw 58, now shown in solid, would be in a different relative position within hole 56. After plate 10 is appropriately positioned, screw 58 could be tightened to fix plate 10 to humerus H.

Figure 6A:
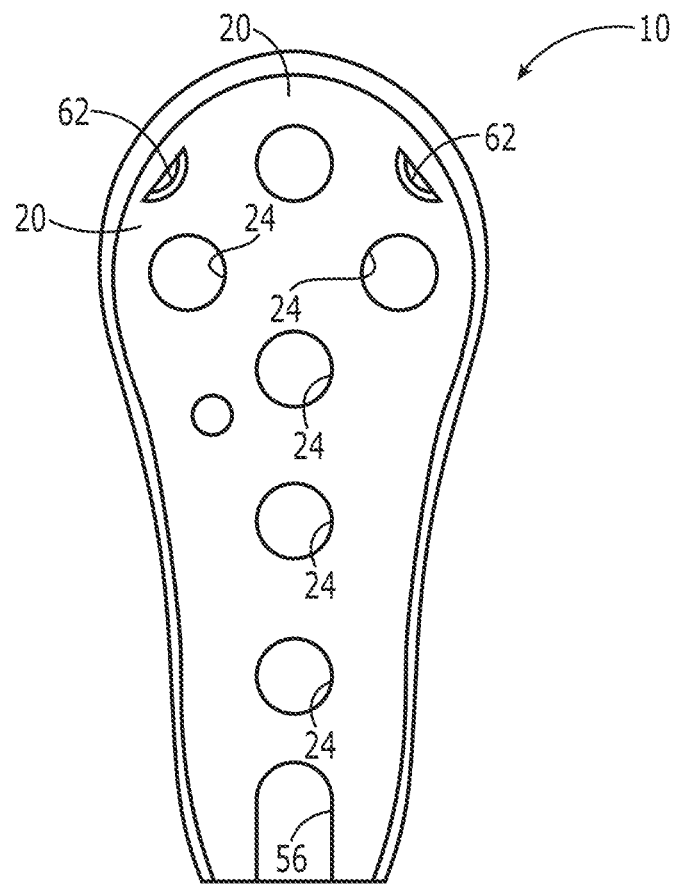
FIG. 6A is a lateral view of an alternative embodiment of the upper section of the proximal humeral fracture plate shown in FIGS. 5A, 5B, 5C, 5D, 5E, 5F. 5G and 5H.
Figure 6B:
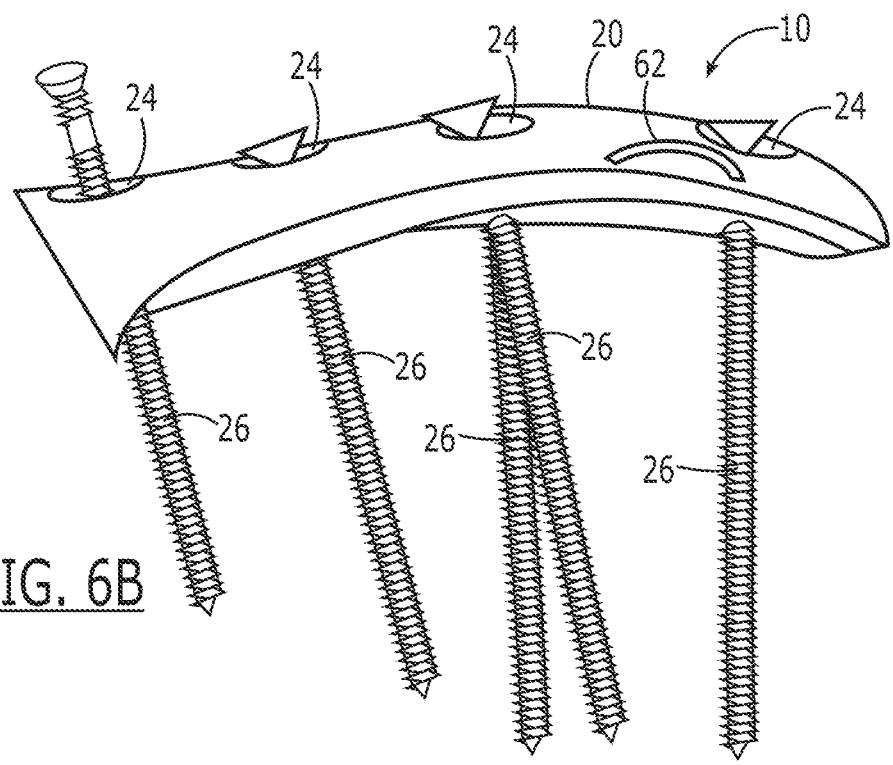
FIG. 6B is a side view of the alternative embodiment of the upper section of proximal humeral fracture plate shown in FIG. 6A.
Figure 6C:
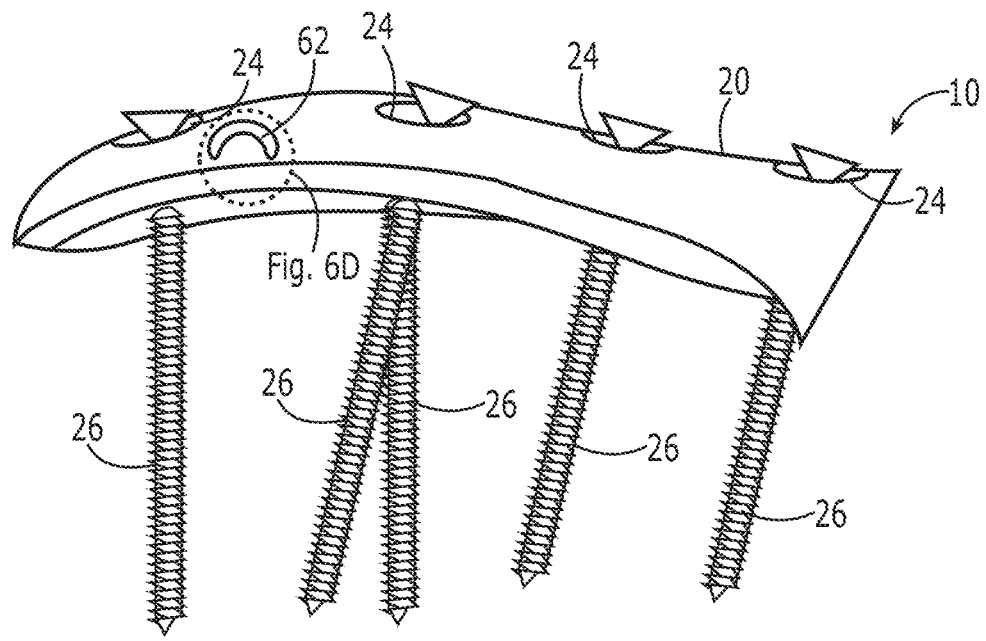
FIG. 6C is a side view of the alternative embodiment of the upper section of proximal humeral fracture plate shown in FIG. 6A.

FIGS. 6A, 6B and 6C illustrate the alternative embodiment of plate 10 further comprising loops 62. Loops 62 allow suture fixation of the rotator cuff to plate 10. FIG. 6A illustrates that a suture S can readily pass through loops 62. FIGS. 6B and 6C illustrate that, optimally, upper section 20 will be sufficiently concave to generally conform to the convex outer shape of a head of humerus H and also appropriate positions for loops 62. Loops 62 could be used in conjunction with one plate, for example plate 10 or 10', or both plates could have loops 62. FIG. 6B also illustrates that screws 26 can be locking screws. As seen by the left most screw 26, which for purposes of illustration, is slightly withdrawn from screw hole 24 to illustrate that screws 26 can be locking screws or non-locking screws.

Figure 6D:
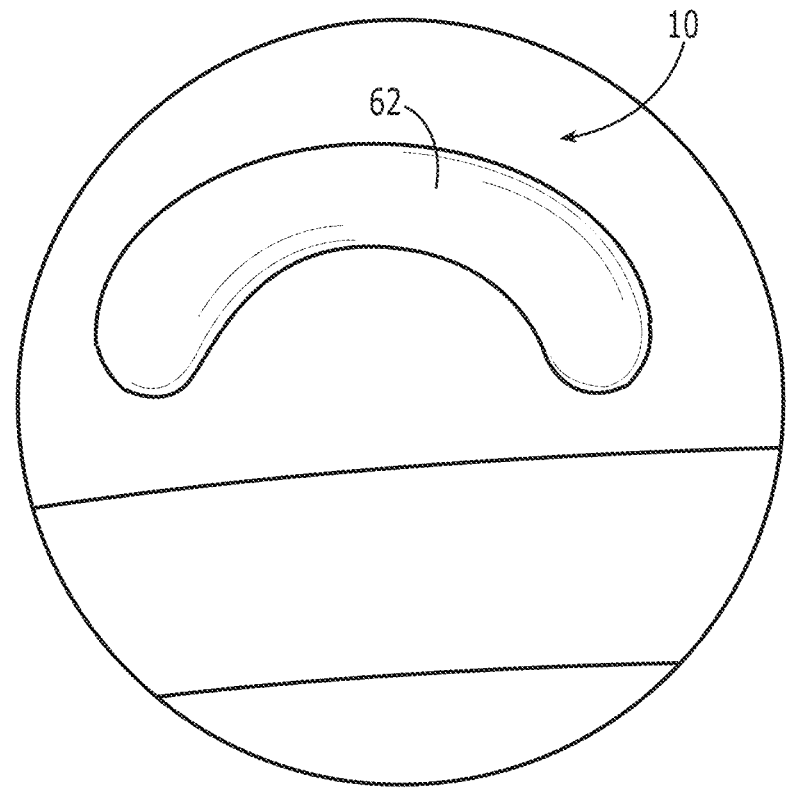
FIG. 6D is a detailed side view of the loop shown in FIG. 6A.

FIG. 6D illustrates loop 62 and further emphasizes that the suture can readily pass through loop 62 and that top of the arch of loop 62 is positioned above upper plate 20. Of course, loop 62 does not have to be arched and this is merely an illustrative example. Irrespective of the shape of loop 62, the suture should be able to readily pass therethrough.

FIG. 7A illustrates a top view of plate 10 fixed to humerus H. Upper section 20 has screw holes 24 for receiving a screw 26 to fix the proximal humerus plate to a head of the left humerus H. As discussed above, the trajectory of the screws 26 are a lateral to medial orientation. While not visible in FIG. 7A, transitional section 30 has holes 34 for receiving screws 36 to fix the transitional section along a lateral cortex of the humerus H. Transitional section 30 is integral with the upper section 20 and is curved sufficiently to avoid a deltoid tuberosity T. A lower section 40, which is also not visible in FIG. 7A, has screw holes 44 for receiving screws 46, the trajectory of screws 46 is an anterior to posterior orientation.

FIG. 7B illustrates a medial view of plate 10 fixed to humerus H. In FIG. 7B, upper section 20 is positioned laterally on humerus H and is not visible because, from this viewing position, it is on the opposite side of humerus H. While upper section 20 is not visible (and therefore shown in dashed), the trajectories of screws 26 are generally in a lateral to medial orientation. Screw holes 34 receive screws 36 to fix the transitional section along a lateral cortex of the humerus H. Transitional section 30 is integral with the upper section 20 and is curved sufficiently to avoid a deltoid tuberosity T. Lower section 40 has screw holes 44 for receiving screws 46, the trajectory of screws 46 is an anterior to posterior orientation. Lower section 40 is integral with the transitional section 30.

Figure 7C:
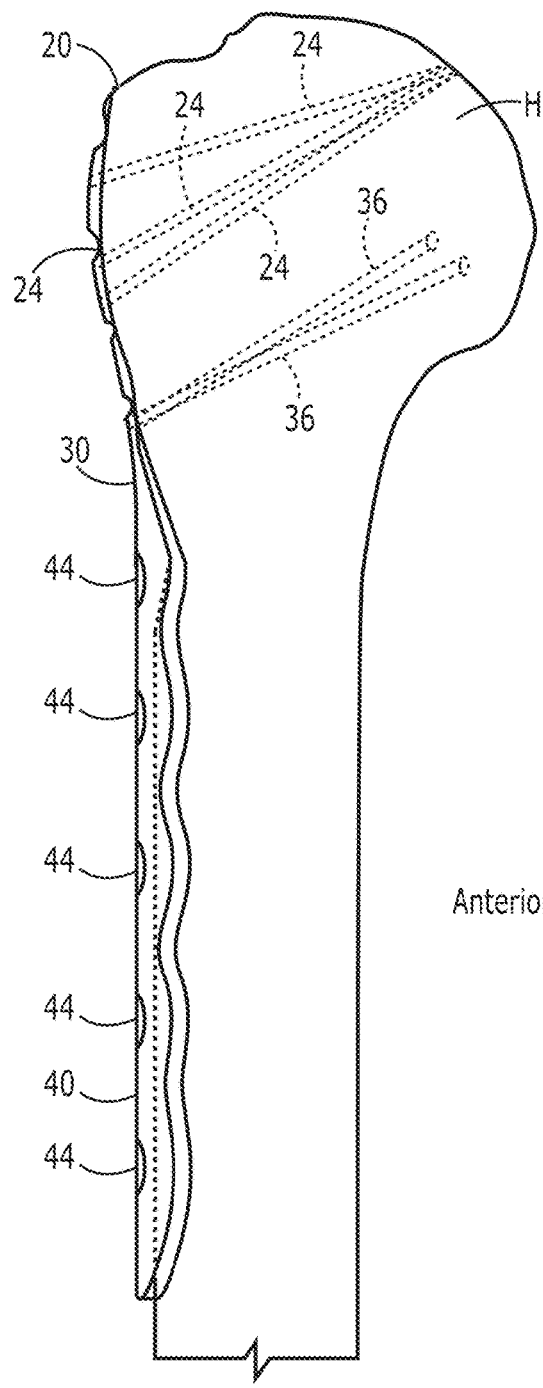
FIG. 7C is a perspective view of the proximal humeral fracture plate shown in FIGS. 7A and 7B.

FIG. 7C illustrates an anterior view of plate 10 fixed to humerus H. As discussed above, plate 10 has upper section 20, transitional section 30 and lower section 40. As also discussed above upper section 20 has holes 24 that receive screws 26 the trajectories of screws 26 are in a lateral to medial orientation. Screw holes 34 receive screws 36 to fix the transitional section 30 along a lateral cortex of the humerus H. Transitional section 30 is integral with the upper section 20 and is curved sufficiently to avoid deltoid tuberosity T. Lower section 40 has screw holes 44 for receiving screws 46, the trajectory of screws 46 is an anterior to posterior orientation. Lower section 40 is integral with the transitional section 30. It is particularly apparent from FIG. 7C that screws 26, 36 and 46 do not have the same trajectories.

Figure 7D:
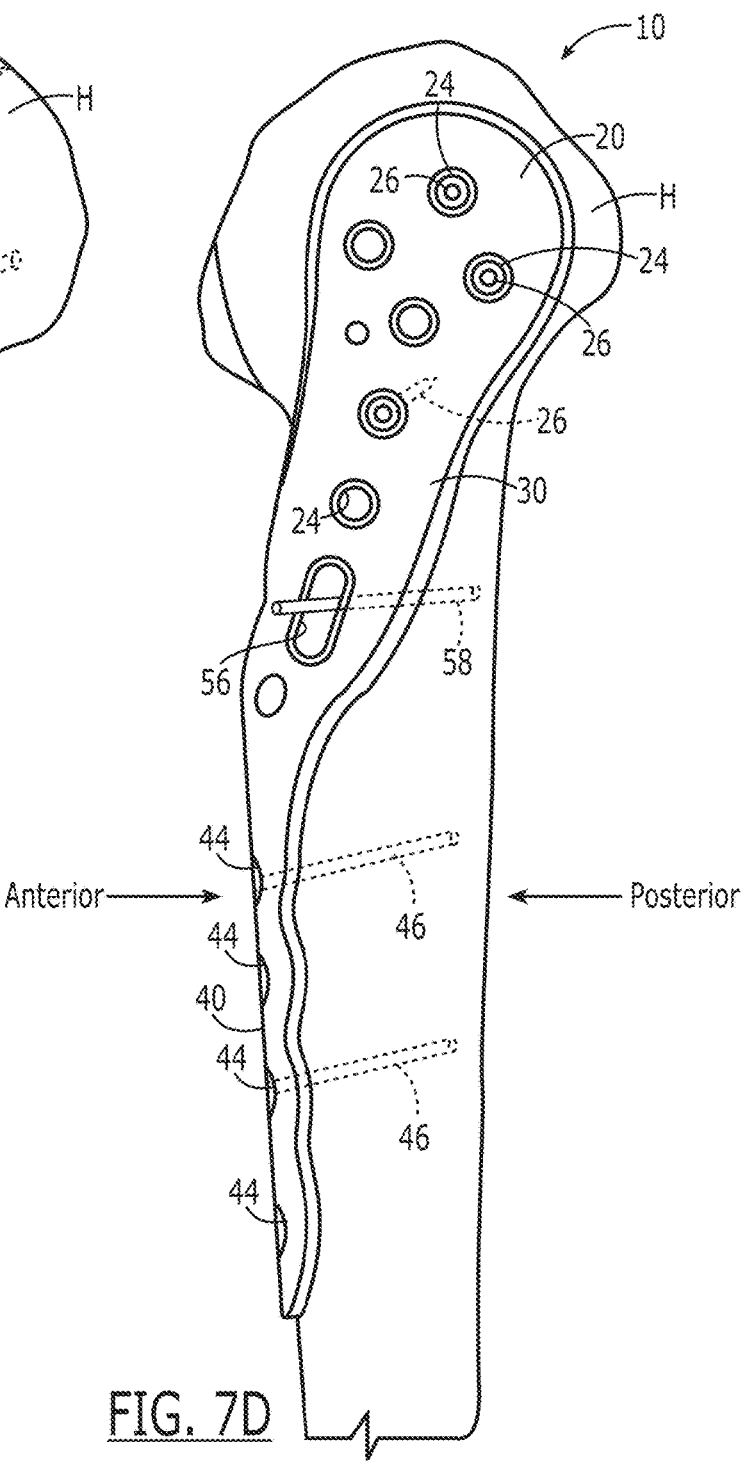
FIG. 7D is a perspective view of the proximal humeral fracture plate shown in FIGS. 7A, 7B and 7C.

FIG. 7D illustrates a lateral view of plate 10 fixed to humerus H. As discussed above, plate 10 has upper section 20, transitional section 30 and lower section 40. As also discussed above upper section 20 has holes 24 that receive screws 26 the trajectories of screws 26 are in a lateral to medial orientation. Screw holes 34 receive screws 36 to fix the transitional section 30 along a lateral cortex of the humerus H. Transitional section 30 is integral with the upper section 20 and is curved sufficiently to avoid deltoid tuberosity T. Lower section 40 has screw holes 44 for receiving screws 46. The trajectory of the screws 26 are in an anterior to posterior orientation. Lower section 40 is integral with the transitional section 30. It is particularly apparent from FIG. 7D that screws 26, 36 and 46 do not have the same trajectories.

Figure 7E:
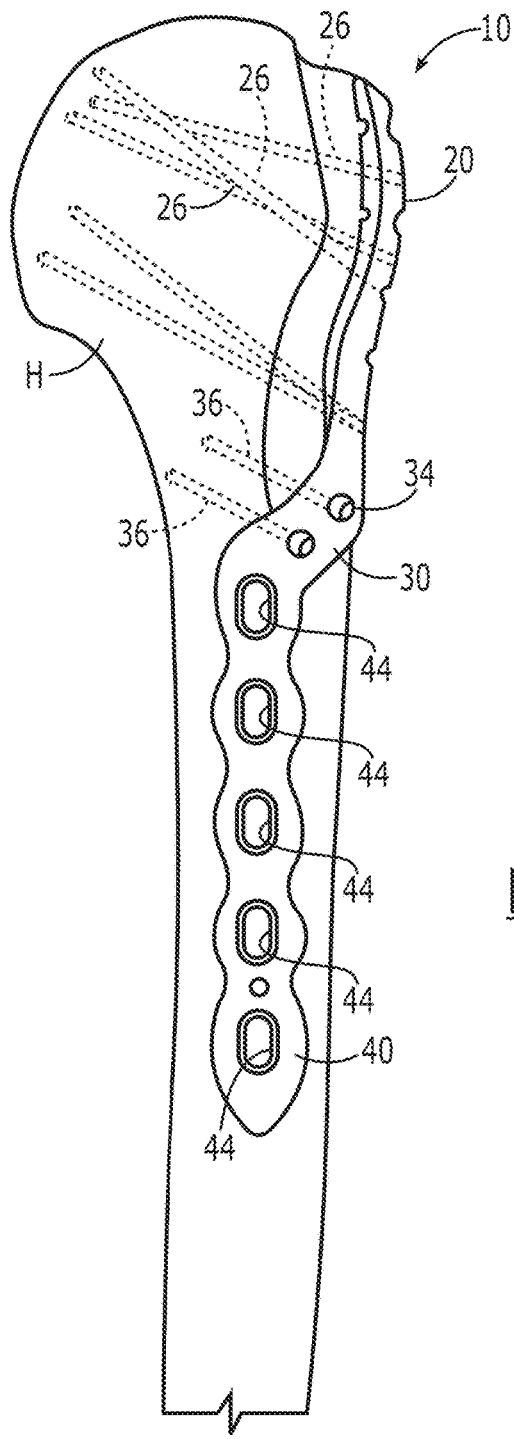
FIG. 7E is a perspective view of the proximal humeral fracture plate shown in FIGS. 7A, 7B, 7C and 7D.

FIG. 7E illustrates a posterior view of plate 10 fixed to humerus H. As discussed above, plate 10 has upper section 20, transitional section 30 and lower section 40. As also discussed above, upper section 20 has holes 24 that receive screws 26. The trajectories of screws 26 are in a lateral to medial orientation. Screw holes 34 receive screws 36 to fix the transitional section 30 along a lateral cortex of the humerus H. Transitional section 30 is integral with the upper section 20 and is curved sufficiently to avoid deltoid tuberosity T. Lower section 40 has screw holes 44 for receiving screws 46, the trajectory of screws 46 are in an anterior to posterior orientation. Lower section 40 is integral with the transitional section 30. It is particularly apparent from FIG. 7E that screws 26, 36 and 46 do not have the same trajectories.

Figure 7F:
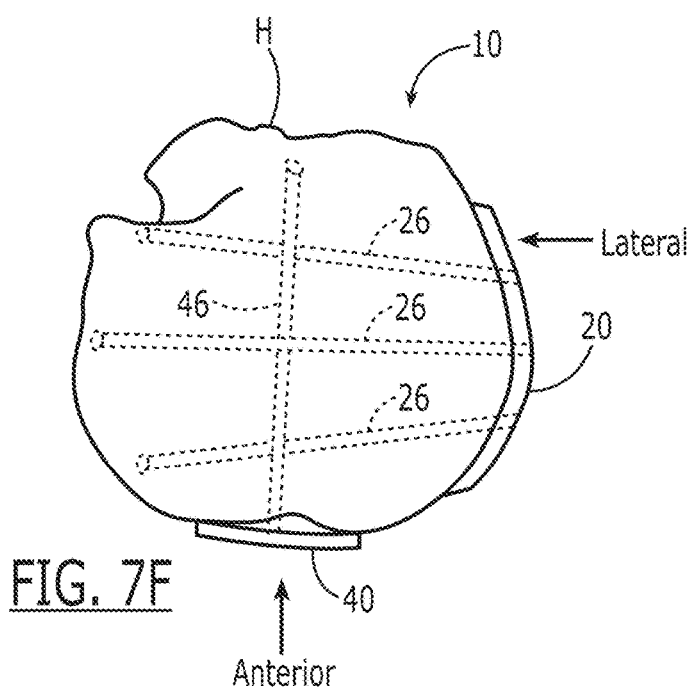
FIG. 7F is a superior view of the proximal humeral fracture plate shown in FIGS. 7A, 7B, 7C, 7D and 7E.

FIG. 7F illustrates a superior view of plate 10 fixed to humerus H. As discussed above, plate 10 has upper section 20, transitional section 30 (not shown in FIG. 7F) and lower section 40. As also discussed above, upper section 20 has holes 24 (not shown in FIG. 7F) that receive screws 26, the trajectories of screws 26 are in a lateral to medial orientation. Lower section 40 has screw holes 44 (not shown in FIG. 7F] for receiving screws 46. The trajectory of screw holes 24 and screws 26 are in an anterior to posterior orientation. Lower section 40 is integral with the transitional section 30. It is particularly apparent from FIG. 7F that screws 26 and 46 do not have the same trajectories and are preferably perpendicular to each other. Screws 36 are not shown in FIG. 7F.

Figure 8:
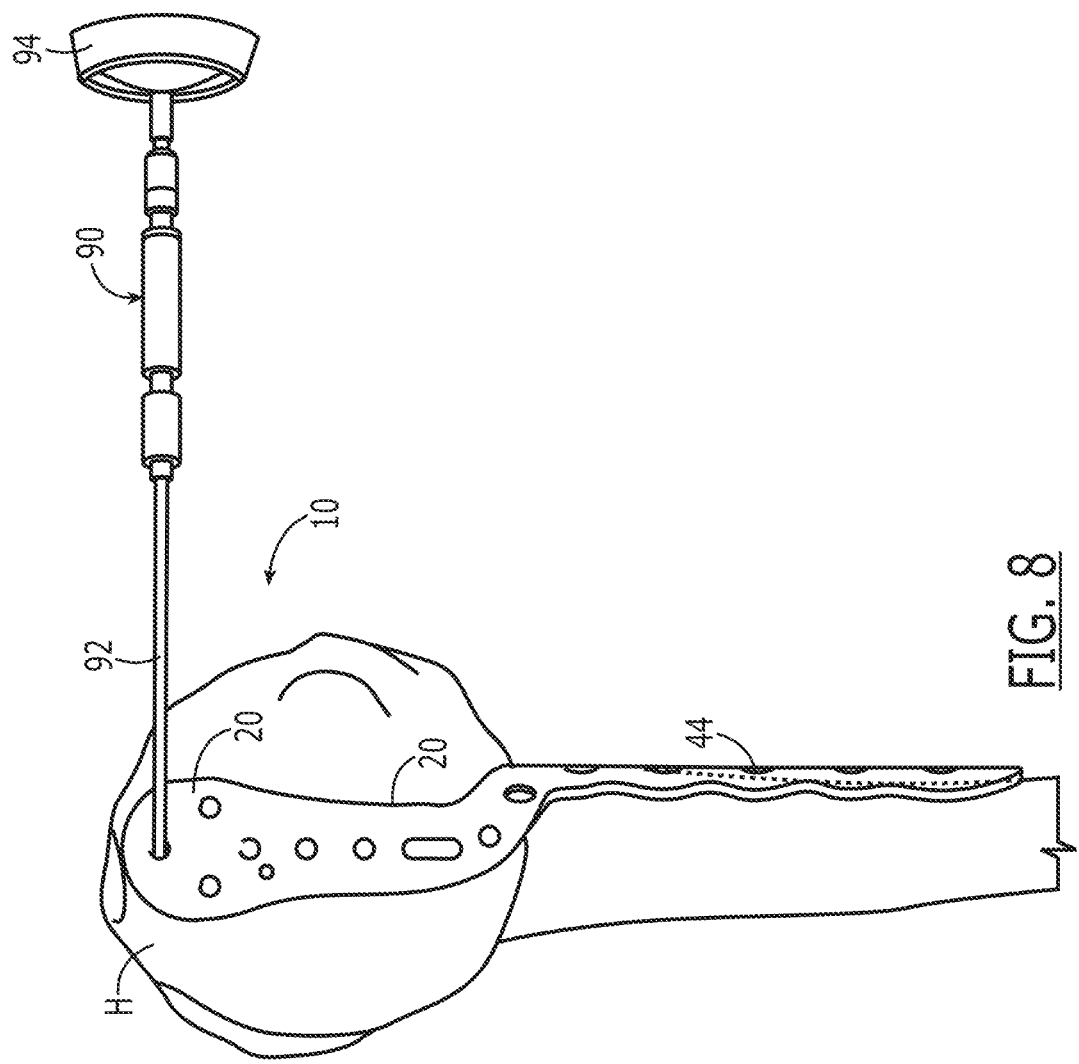
FIG. 8 is a perspective view of an external targeting arm used to facilitate fixation of the proximal humeral plate to the patient's shoulder.

FIG. 8 illustrates an external targeting arm 90 is used to facilitate fixation of the proximal humeral plate 10 to the patient's shoulder. External targeting arm 90 has locking guide 92 and driver 94. In order to place screw 26 through screw holes 24, the surgeon makes a small incision through the deltoid to access plate 10. Locking guide 92 is passed therethrough the deltoid and mates with screw hole 24 to form a pathway to guide screw 26 such that screw 26 can be used to fix plate 10 to the patient's humerus. This process can be repeated to allow the surgeon to place sufficient screws 26, 36 and 46 to appropriately fix plate 10 to humerus H. Typically, the surgeon's screw placement can be guided fluoroscopically or any other alternative means. This is preferred because the deltoid is not required to be detached for this process. In addition, the patient's arm is not, generally speaking, moved or rotated to place screws 26, 36, 46. As discussed above, movement of the patient's arm can negatively affect the surgery because it can result in loss of reduction.

When referring to the trajectory or orientation of screws or screw holes, it should be understood that trajectory or orientation is not exact and that screws or screw holes that are generally in a particular trajectory or orientation are within this description. For example, in FIG. 7F, screws 26 are generally in a lateral to medial orientation or trajectory. Because screws 26 are generally in a lateral to medial orientation, they are considered to have a lateral to medial orientation. The same holds true for other screws and screw holes of this application. As discussed above, upper section 20 has holes 24 that receive screws 26. The trajectories of screws 26 are in a lateral to medial orientation. However, screws 26 may be angled slightly such that they are not exactly co-linear with the lateral to medial orientation of screw hole 24. Screw holes 34 receive screws 36 to fix the transitional section 30 along a lateral cortex of the humerus H. As with screws 26, screws 36 may be slightly angled. Lower section 40 has screw holes 44 for receiving screws 46, the trajectory of screws 46 are in an anterior to posterior orientation. As with screws 26 and 36, screws 46 may be slightly angled. Lower section 40 is integral with the transitional section 30. While the orientation of the trajectory of screw holes 24, 34 and 33 have been described, screw holes 24, 34 and 44 are sized such that screws 26, 36 and 46 can be angled to have a path that is five, ten or even fifteen degrees or more from the orientation of the trajectory of the respective screw hole that the screw passes therethrough. Phrased differently, as seen in FIG. 7B, screws 46 are not parallel because each screw 46 has been angled slightly differently through its respective screw hole 44.

While the invention has been illustrated and described in detail in the drawings and description, the same is to be considered as an illustration and is not limited to the exact embodiments shown and described. All equivalents, changes and modifications that come within the spirit of the invention are also protected by the claims that are set forth below.

What we claim is:

1. A fracture plate for promoting healing of a fracture of a human bone, comprising:
   (a) an upper section having at least one screw hole for receiving an upper screw, the trajectory of the screw hole is a lateral to medial orientation;
   (b) an anteriorly-curved middle section having a plurality of screw holes for receiving a plurality of middle screws, the middle section integral with the upper section, the plurality of screw holes therethrough the middle section having an oblique trajectory relative to the trajectory of the screw hole of the upper section and configured to match an anatomy of the bone wherein one or more of the plurality of screw holes therethrough the middle section each have a more anterior to posterior trajectory than the screw hole therethrough the middle section immediately above it; and
   (c) a lower section having at least one screw hole for receiving a lower screw, the trajectory of the screw hole having an oblique trajectory relative to the trajectory of the plurality of screw holes of the middle section, the lower section integral with the middle section.

2. The fracture plate of claim 1, further comprising: the at least one screw hole of the upper section is a plurality of screw holes.

3. The fracture plate of claim 2, further comprising: the plurality of screw holes of the middle section comprises at least one circular screw hole suitable to receive a middle screw, the at least one screw hole sized to permit the fracture plate to be positioned not to project beyond the end of the bone.

4. The fracture plate of claim 3, further comprising: at least one of the screw holes of the middle section comprises a circular or oval screw hole capable of receiving the middle screw, wherein the middle screw received by the circular screw hole is a locking screw or a compression screw.

5. The plate of claim 4, further comprising: the at least one screw hole of the upper section is four screw holes.

6. The fracture plate of claim 5, further comprising: wherein the four screw holes of the upper section are each configured to receive a screw.

7. The fracture plate of claim 6, further comprising: the four screw holes are symmetrically disposed along the longitudinal axis of the upper section.

8. The fracture plate of claim 7, further comprising: the at least one screw hole of the lower section is another plurality of screw holes.

9. The fracture plate of claim 8, further comprising: the another plurality of screw holes of the lower section is selected from the group consisting of three screw holes, four screw holes, or five screw holes.

10. The fracture plate of claim 9, further comprising: a plurality of locking screws, wherein the another plurality of screw holes of the lower section are configured to receive one of the locking screws.

11. The fracture plate of claim 1, further comprising: the middle section is anteriorly curved and conforms to the lateral cortex of the bone.

12. The fracture plate of claim 11, further comprising: the plurality of screw holes therethrough the middle section comprises two screw holes.

13. The fracture plate of claim 1, further comprising: each of the plurality of screw holes therethrough the middle section having a more anterolateral to posteromedial trajectory than the screw hole above it.

14. The fracture plate of claim 1, further comprising: the upper section is configured to conform to the anatomy of a head of the bone.

15. The fracture plate of claim 14, further comprising: the at least one screw hole of the upper section is a plurality of screw holes.

16. The fracture plate of claim 15, wherein the plurality of screw holes of the upper section have parallel trajectories.

17. The fracture plate of claim 15, wherein the plurality of screw holes of the upper section have non-parallel trajectories.

18. The fracture plate of claim 17, wherein screw holes of the upper section each receive an upper screw configured for fastening the upper section of the plate to the head of the bone are in different planes.

19. The fracture plate of claim 1, wherein the fracture plate is precontoured such that the screw holes of the fracture plate are not deformed during fixation of the fracture plate to the bone so as to compromise screw fixation to the bone.

* * * * *